US006563575B1

(12) United States Patent
Nichols et al.

(10) Patent No.: US 6,563,575 B1
(45) Date of Patent: May 13, 2003

(54) OPTICAL SENSING SYSTEM FOR DETECTING WELDS AND DEFECTS IN METAL

(75) Inventors: Randall William Nichols, Denver, CO (US); Kenneth Wayne Maydew, Nederland, CO (US)

(73) Assignee: Automated Technology Services, Inc., Nederland, CO (US)

( * ) Notice: Subject to any disclaimer, the term of this patent is extended or adjusted under 35 U.S.C. 154(b) by 286 days.

(21) Appl. No.: 09/636,482

(22) Filed: Aug. 10, 2000

Related U.S. Application Data

(60) Provisional application No. 60/148,106, filed on Aug. 10, 1999.

(51) Int. Cl.[7] ............................................. G01N 21/86
(52) U.S. Cl. ............................. 356/237.1; 356/237.2; 356/445
(58) Field of Search ............................. 356/445, 446, 356/448, 237.1, 237.2, 394, 239.7, 429–431, 600; 382/147–150; 403/270; 73/850

(56) References Cited

U.S. PATENT DOCUMENTS 4,734,766 A * 3/1988 Shiozumi et al. ........... 356/608
5,150,175 A * 9/1992 Whitman et al. ............ 356/429
5,701,181 A * 12/1997 Boiarski et al. ............ 250/227.2

OTHER PUBLICATIONS

Roland Weld Seam Detector Operating Instructions.

Roland Weld Seam Detection Diagrams.

* cited by examiner

*Primary Examiner*—Hoa Q. Pham
*Assistant Examiner*—Vincent Barth
(74) *Attorney, Agent, or Firm*—Jennifer L. Bales; Macheledt Bales LLP

(57) ABSTRACT

An optical sensing system for detecting welds and defects in metal brightly illuminates a broad section of the metal and images a swath of the metal onto a multi-element detector array, generating voltage signals representing the reflectivity of the swath of the metal as it passes under the detector. A processor system detects areas of low reflectivity and indicates a defect. A slit mask placed in front of the detector array narrows the imaged swath to reduce false accepts. A color filter in front of the detector array reduces ambient light interference. The processor system incorporates an auto-calibration function to compare the current signal to an averaged reference signal.

10 Claims, 2 Drawing Sheets

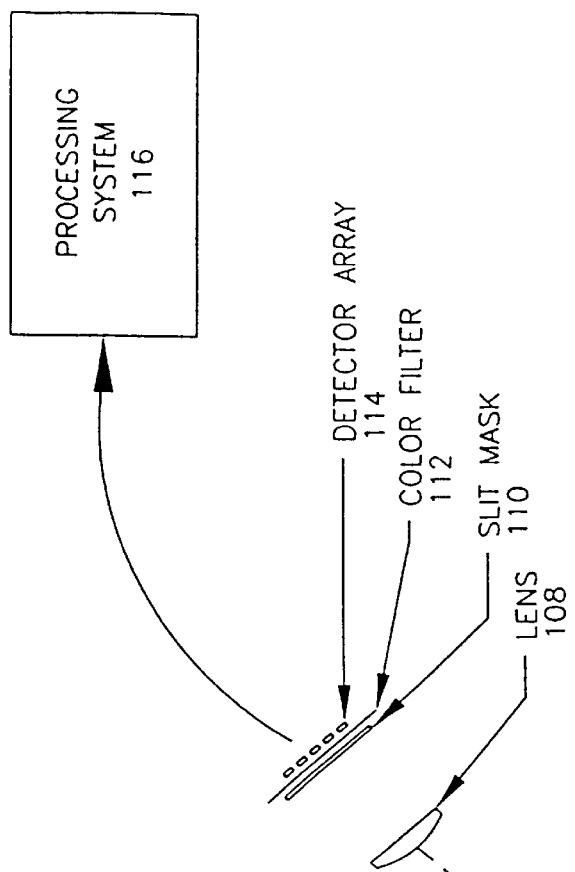
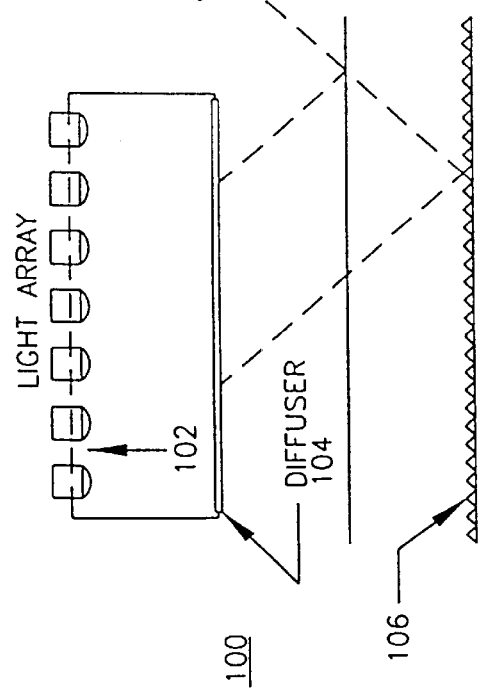
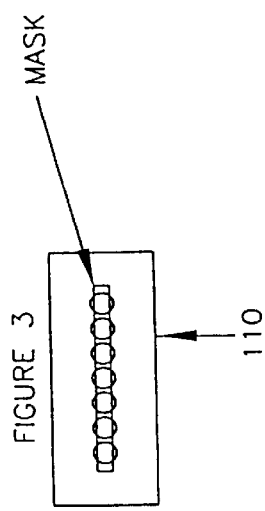
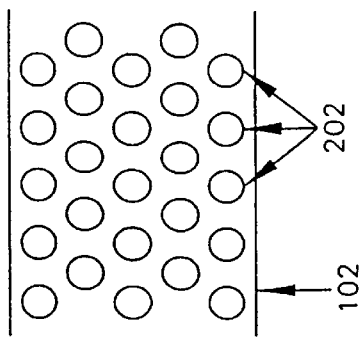

OPTICAL SENSING SYSTEM FOR DETECTING WELDS AND DEFECTS IN METAL

BACKGROUND OF THE INVENTION

This application claims the benefit of U.S. Provisional Application No. 60/148,106, filed Aug. 10, 1999.

FIELD OF THE INVENTION

The present invention relates to apparatus and methods for detecting defects in reflective material, such as weld splices in metal rolls or coils.

DESCRIPTION OF THE PRIOR ART

Weld splices in tin plated steel coils (rolled up sheets) pose a problem in the can making and other industries that run the material into presses, slitters, or other forming equipment. Welds in a steel coil are harder than the steel coil itself, and may damage tooling when fed into a press. The weld may also result in defective products, such as a weld running across a finished can lid. This would result in an area without protective lacquer, as well as being cosmetically unacceptable. In addition, it is often necessary to locate a weld in order to properly position metal, for example to avoid a weld in a steel drum when attaching a handle or adding a painted label.

Inductive eddy current based sensors are currently used as weld splice detectors, thickness gauges, and double sheet detectors. They can detect a lap weld (overlap) of sufficient mass to effect an inductive change. However, modern welding techniques have moved toward narrow lap splices and butt splices, which do not result in sufficiently changed inductance to detect the weld in this manner.

Vision systems comprising video cameras, frame grabbers, computers, and the like accomplish gray scale comparisons in an attempt to detect welds. These are prohibitively expensive for the task, and not reliable enough.

A need remains in the art for a reliable, inexpensive system for detecting welds and other imperfections in metals.

SUMMARY OF THE INVENTION

It is an object of the present invention to provide a reliable, inexpensive sensing system for detecting welds and other imperfections in metals. The present invention includes a multi-element solid state diffuse light source capable of illuminating a broad section of metal. Light from the metal surface is focussed by a lens and detected by a multiple element array of light detectors, which is masked by a narrow slit aperture. The combination of the diffuse light source, appropriate lens selection, narrow slit aperture, and multiple detectors allows for uninterrupted inspection of a moving sheet of metal, even with appreciable changes in distance and angle between the metal and the detector array.

The present invention utilizes a multi-element linear detector array capable of redundant inspections in order to reduce the probability of false accepts from, for example, spotty or inconsistent defects. Since a weld forms a generally dark, dull line, but may include shiny spots, a single detector would give a false positive if it detected a shiny spot within a weld. Similarly, the narrow slit aperture ensures that only light reflected from the weld itself is detected, rather than light from the shiny portions next to the weld. Thus false positives resulting from averaging the small amount of light reflected from the weld with the shiny portions are avoided.

The signals from the linear detector array are passed to a processor system, which analyzes the signals to determine when a weld is passing under the sensing system. The processor system also includes a self calibration feature, which provides an accurate reference signal to compare against the signal being analyzed. A color filter is used to prevent ambient light from interfering with the detection process.

BRIEF DESCRIPTION OF THE DRAWINGS

FIG. 1 shows a side view of an optical sensing system according to the present invention.

FIG. 2 shows a bottom view of the light array of FIG. 1 with the diffuser removed.

FIG. 3 shows a bottom view of the slit mask of FIG. 1.

DETAILED DESCRIPTION OF THE PREFERRED EMBODIMENT

Figure 4:
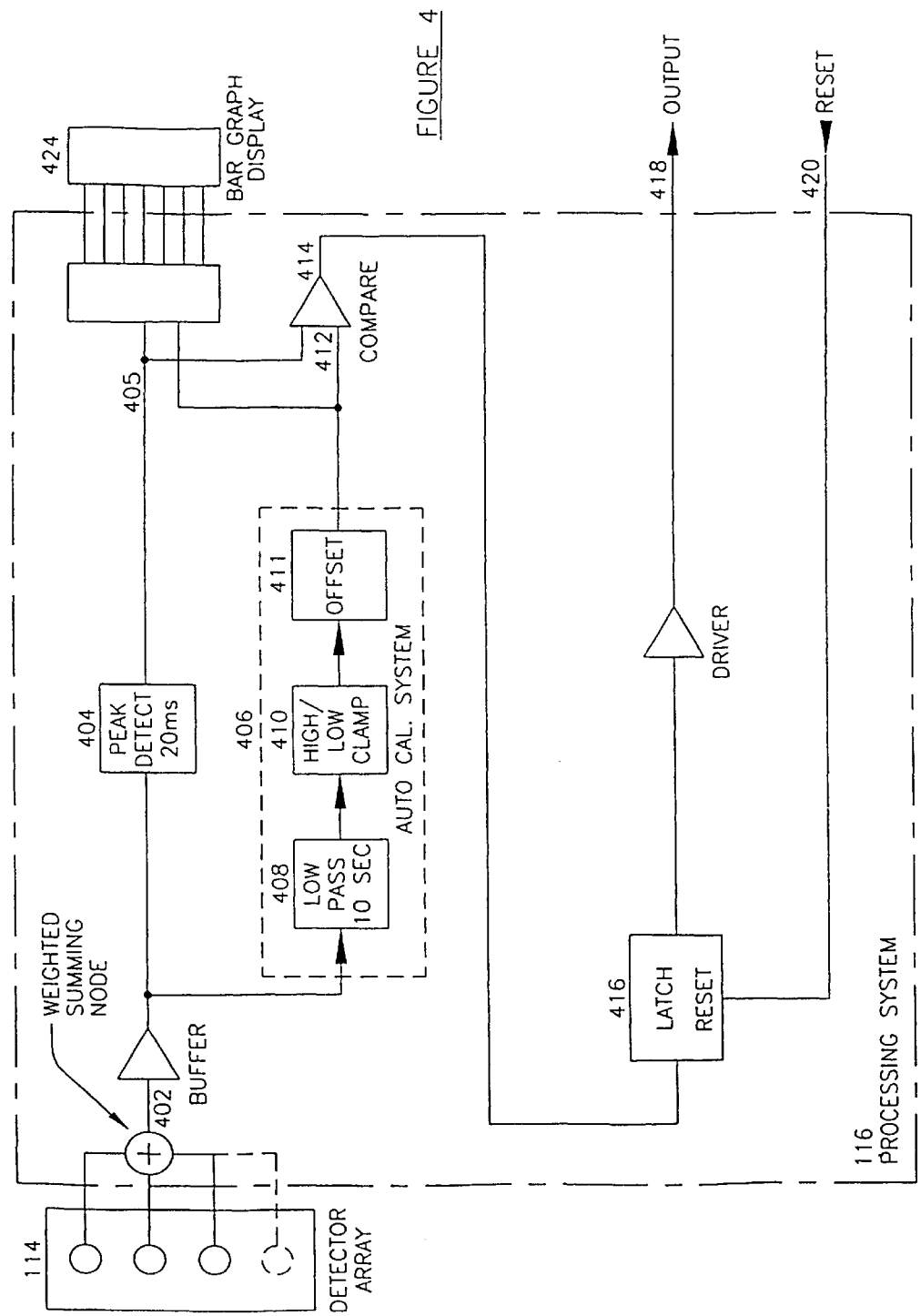
FIG. 4 is a system block diagram of the processing system associated with the optical sensing system of FIG. 1.

FIG. 1 shows a side view of an optical sensing system 100 for inspecting flat metal surface 106 for welds or other defects. Multi-element solid state light array 102 provides light which passes through diffuser 104 and illuminates a large area of metal 106. This broad coverage helps accommodate changes in the position and angle of metal 106 with respect to optical sensing system 100.

Lens 108 projects an image of metal 106 onto slit mask 110. Preferably, the lens (and/or other optics) is chosen to provide a large depth of focus, so that the image is sharp even if the distance between the metal and the detector array varies. Slit mask 110 has a narrow slit opening, and thus allows only a narrow field of inspection. This allows detection of only the dark, dull weld itself, rather than averaging in shiny portions on either side of the weld. FIG. 3 shows a bottom view of slit mask 110. It is important that only a narrow swath be inspected at one time, to prevent surrounding reflective areas from masking the weld. Color filter 112 filters out most of the ambient light, which will, for the most part, not have the same wavelength as the light source.

Detector array 114 detects the image projected by lens 108, through mask 110 and filter 112, and generates a voltage signal that is proportional to the amount of light detected by each detector. These signals are passed to processing system 116, for analysis. FIG. 4 shows how processing system 116 analyzes the signals to detect welds.

FIG. 2 shows a bottom view of light array 102 with diffuser 104 removed, showing the array of LEDs 202 comprising the light source. Once diffuser 104 is placed over light array 102, the light diffuses and merges into a smooth sheet of light covering a broad swath of the metal. Those skilled in the art will appreciate that various other light sources providing a smooth swath of light may be used. For example, fluorescent and incandescent light sources may be used.

FIG. 3 shows a bottom view of slit mask 110 placed over detector array 114 (color filter 112 is not shown). The slit is oriented to allow the image of a thin stripe of metal 106 to reach detector array 114. The thin stripe is oriented across the metal as it passes under optical sensing system 100, so that all of the metal is imaged and analyzed as the metal passes under system 100. The slit is narrow in order to allow only the image of the weld to be detected by the detector array 114 as it passes. Thus, false positives resulting from averaging the small amount of light reflected from the weld with the shiny portions on either side of the weld are avoided. An array of detectors is used, so that a shiny spot within a weld does not produce a false positive.

FIG. 4 is a system block diagram of processing system 116. The voltages provided by detector array 114 (which are proportional to the amount of light detected by each detector, which is in turn related to the reflectivity of the portion of metal 106 imaged onto that detector) are provided to weighted summing node 402. Node 402 is weighted for increased sensitivity to a detector signal significantly lower than the average detector output. A low signal represents a possible defect (or decrease in reflectivity) in the metal being inspected. Thus, if any detector detects a low enough signal to indicate a defect, it will outweigh other detectors-not seeing the defect, and generate a pulse, indicating that a weld has been sensed. Peak detector 404 acts as a valley stretcher. It increases the time signature of a defect pulse. This provides a signal which is long enough to analyze. The output 405 of peak detector 404 is called the real time voltage.

Auto calibration system 406 generates a reference signal 412 against which to compare real time signal 405 to detect defects. It includes a lowpass filter 408 having a long time constant (e.g. 10 seconds). This averages the signal that is seen over time, to provide an average signal. Offset block 411 shifts the average signal so that reference signal 412 holds comparator 414 in the off position. In the event of a real time defect, real time voltage 405 is high enough to override the averaged offset voltage and drive comparator 414 output high. The variation in the possible voltage of reference signal 412 is limited by high/low clamp 410, for example in order to cause a misaligned sensor to indicate a failure rather than improperly adjusting reference signal 412.

When the comparator 414 output becomes active, indicating a detected defect, latch 416 holds output 418 in the error state, until it is externally reset by reset 420.

A bar graph display 424 (or other types of display) may be used as a visual indicator of the computer output state. Thus, the status of such factors as sensitivity, range, and verification of proper operation may be observed.

While the exemplary preferred embodiments of the present invention are described herein with particularity, those skilled in the art will appreciate various changes, additions, and applications other than those specifically mentioned, which are within the spirit of this invention. For example, while the preferred embodiment uses a solid state diffuse light array as the light source, other sources of bright diffuse light may be used. In addition, the processing system may apply other algorithms to detect a weld, for example summing and comparing detector signals rather than considering one dark spot as indicating a weld.

What is claimed is:

1. A sensing system for detecting welds in a metal surface comprising:
   a diffuse light source capable of illuminating a broad section of the metal surface;
   a multiple element linear array of light detectors, the detector array generating a response proportional to the amount of light detected by each detector;
   a lens for focussing light reflected from the metal surface toward the light detector array; and
   a processor connected to the light detector array for observing and analyzing the detector array response;
   wherein the processor further includes a weld determining element for determining a weld is passing under the sensing system when the processor observes an unusually low response from a detector.

2. The sensing system of claim 1, wherein the processor further includes a signal generating element for generating an indicating signal responsive to the weld determining element.

3. The sensing system of claim 2, wherein the processor further includes a display for displaying a message responsive to the indicating signal.

4. The sensing system of claim 1, further comprising a slit aperture mask placed between the lens and the detector array.

5. The sensing system of claim 1, further comprising a color filter placed between the lens and the detector array.

6. The sensing system of claim 1, wherein the processor further includes means for self calibrating.

7. A sensing and analyzing system for detecting welds and imperfections in a metal surface comprising:
   a diffuse light source capable of illuminating a broad section of the metal surface;
   a multiple element linear array of light detectors, the detector array generating a response proportional to the amount of light detected by each detector;
   a slit aperture mask placed between the lens and the detector array;
   a lens for focussing light reflected from the metal surface on the slit aperture mask; and
   a processor connected to the detector array for observing and analyzing the detector array response and including means for determining when a weld is passing under the sensing system based upon the detector array response;
   wherein the processor further includes means for generating a weld indicating signal responsive to the determining means.

8. The system of claim 7, wherein the determining means determines that a weld is passing under the sensing system based upon an unexpectedly low response from at least one detector in the detector array.

9. The sensing system of claim 7, further comprising a color filter placed between the lens and the detector array.

10. The sensing system of claim 7, wherein the processor further includes means for self calibrating.

\* \* \* \* \*